United States Patent [19]

Varn

[11] Patent Number: 5,224,925
[45] Date of Patent: Jul. 6, 1993

[54] FOOT SPLINT

[75] Inventor: Harold T. Varn, Lawrenceville, Ga.

[73] Assignee: L'Nard Associates, Inc., St. Petersburg, Fla.

[21] Appl. No.: 898,573

[22] Filed: Jun. 15, 1992

[51] Int. Cl.$^5$ .............................................. A61F 3/00
[52] U.S. Cl. ......................................... 602/28; 602/27; 602/23
[58] Field of Search ................... 602/27, 28, 29, 12, 602/23; 36/151, 160; 128/60 H, 60 E

[56] References Cited

U.S. PATENT DOCUMENTS

| 830,894 | 9/1906 | Garrod | 602/27 |
|---|---|---|---|
| 1,638,285 | 8/1927 | Brooks | 602/27 |
| 3,976,059 | 8/1976 | Lonardo | 602/28 |
| 5,014,690 | 5/1991 | Hepburn et al. | 602/27 X |

Primary Examiner—Richard J. Apley
Assistant Examiner—Beverly A. Meindl
Attorney, Agent, or Firm—Zarley, McKee, Thomte, Voorhees & Sease

[57] ABSTRACT

A plastic foot splint has a back portion, a heel portion, and a foot portion, with the foot portion normally being positioned at a substantial right angle with respect to the leg portion. The splint is of resilient spring-like material to permit the foot portion to be forcibly deflected at the heel portion to create an obtuse angle with respect to the leg portion. A diagonally extending frame connects the heel and foot portions. Expandable means comprising telescopically secured side members allow the frame to maintain its connection between the heel and foot portions when the foot portion is forcibly moved to form an acute angle with respect to the leg portion. Lock elements are on the frame to rigidly hold the foot portion in a preselected obtuse angular relationship with respect to the leg portion.

7 Claims, 3 Drawing Sheets

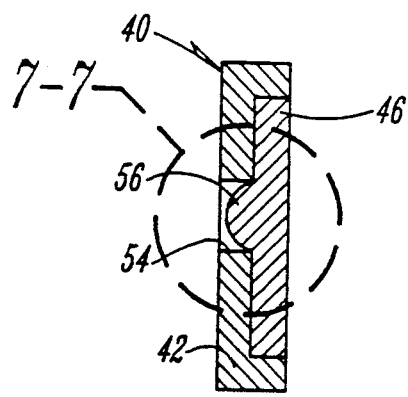
FIG. 6
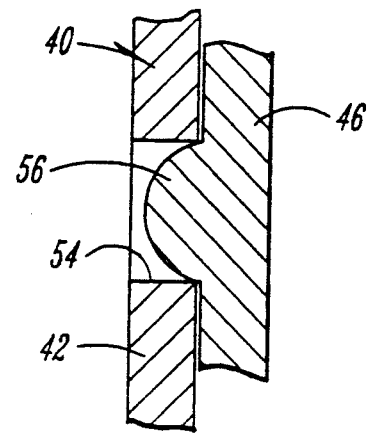
FIG. 7
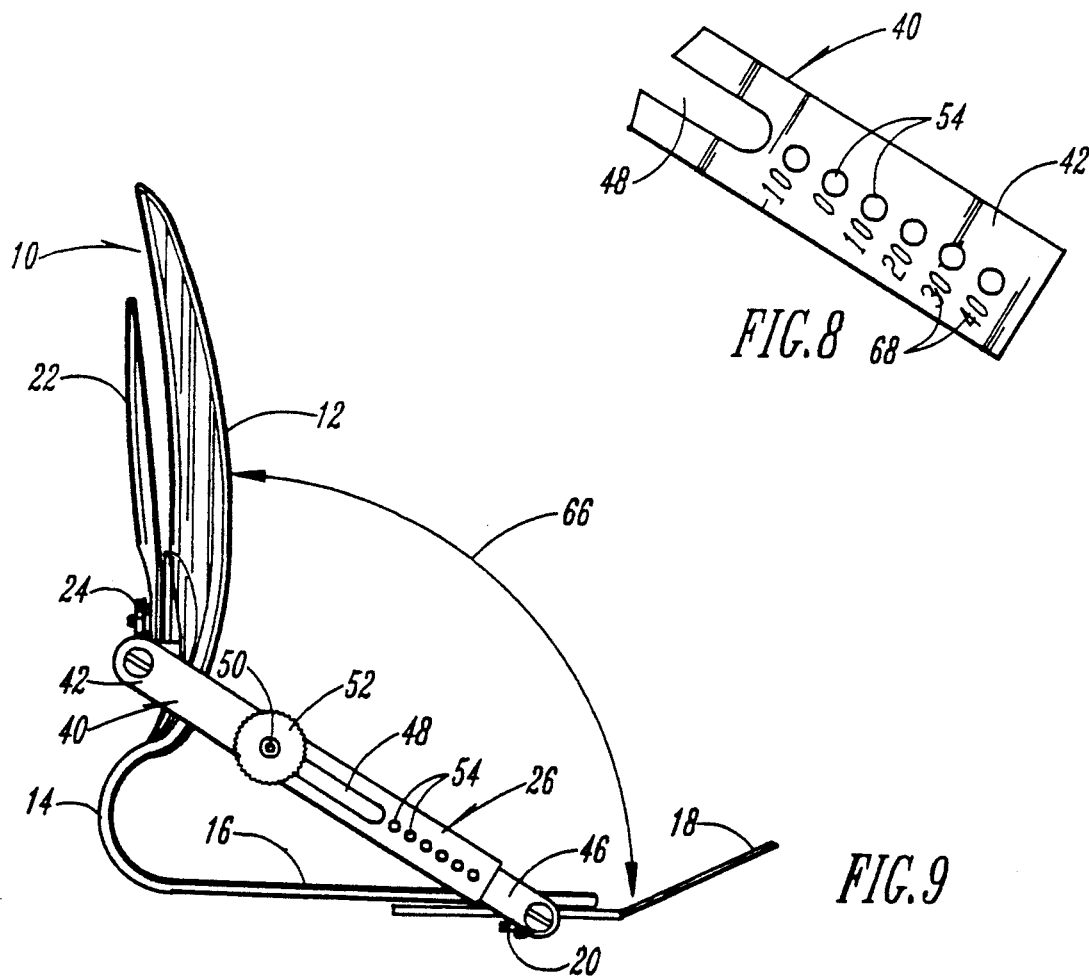
FIG. 8
FIG. 9

FOOT SPLINT

BACKGROUND OF THE INVENTION

Bedfast patients often experience a drop-foot condition wherein the foot is extended and forms an obtuse angle with respect to the leg. If the condition is not rectified, the foot may become rigidly affixed in the extended position which will prevent the patient from walking when out of bed.

Patients suffering from spinal injuries often suffer from the drop-foot condition, and the feet are commonly subjected to spasms as well.

The splint of U.S. Pat. No. 3,976,059 is adapted to deal with the drop-foot condition wherein the inherent spring like characteristics of the splint material tend to draw the extended foot back towards its normal position. However, the use of such a splint to correct the drop-foot situation is extremely slow and there is no way to program the splint to deal with predetermined increments of foot extension.

Commonly, the extended foot is partially subjected to dorsiflexion wherein the foot is partially moved back towards its normal position. The foot is then encased in a rigid cast and left for a period of time whereupon the cast is then removed, additional dorsiflexion is applied, and a new cast is placed on the foot. This process is repeated with a plurality of subsequent casts whereupon the foot is returned to its normal angular position with respect to the leg.

It is therefore an object of this invention to provide a foot splint which can effectively deal with incremental corrections of drop-foot extension without the use of plaster casts.

A further object of this invention is to provide a foot splint which can be adjusted to incremental angular positions and locked in such positions to deal with any angular displacement of the foot being experienced by a given patient.

A still further object of this invention is to provide a foot splint which can be easily moved to and locked to a given position in the process of dealing with drop-foot conditions existing in bedfast patients.

These and other objectives will be apparent to those skilled in the art.

SUMMARY OF THE INVENTION

A plastic foot splint is provided which has a back portion a heel portion, and a foot portion. The foot portion is joined to the back portion by the heel portion and is normally positioned at a substantial right angle with respect to the leg portion.

The splint is comprised of a resilient spring like material to permit the foot portion to be forcibly deflected at the heel portion to create an obtuse angle with respect to the leg portion. The foregoing structure exists in the prior art.

The device of this invention includes a diagonally extending frame which connects the heel and the foot portions. The frame is substantially rectangular in shape and has parallel spaced leg and foot members secured to the leg and foot portions, respectively, and parallel side members connecting the leg and foot members. The side members are telescopically expandable to accommodate different angular positions existing between the foot portion and the leg portion of the splint. A lock means is associated with the side members to hold the side members in various positions to accommodate the angular disposition of the foot portion with respect to the leg portion. A detent means is present on the side members to facilitate the incremental change in position of the side members to accommodate the foregoing situation.

BRIEF DESCRIPTION OF THE DRAWINGS

FIG. 6 is an enlarged scale sectional view taken on line 6—6 of FIG. 3;

FIG. 7 is an enlarged scale sectional view taken on line 7—7 of FIG. 6;

FIG. 8 is a large scale partial elevational view of a portion of the frame member of FIG. 1 taken on lines 8—8 of FIG. 1; and FIG. 9 is a side elevational view of the splint of FIG. 3 shown in a partially extended position.

DESCRIPTION OF THE PREFERRED EMBODIMENT

Figure 1:
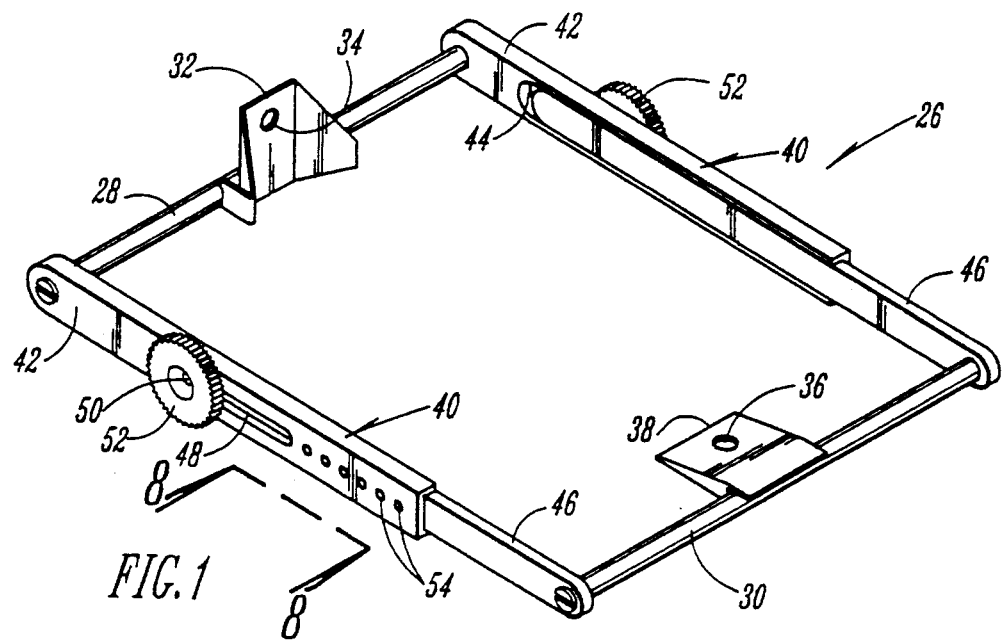
FIG. 1 is a perspective view of the frame which attaches to the foot splint of this invention.
Figure 2:
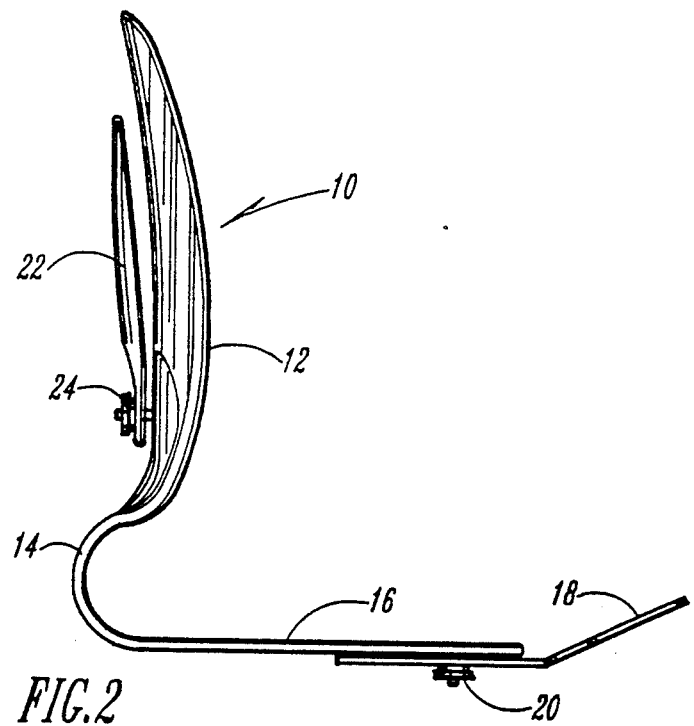
FIG. 2 is a reduced scale side elevational view of the basic plastic splint.
Figure 3:
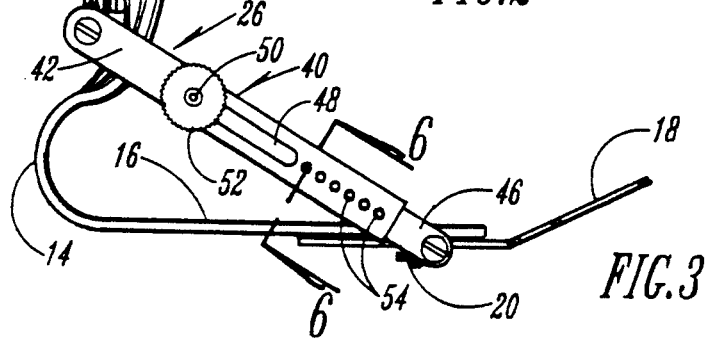
FIG. 3 is a side elevational view similar to that of FIG. 2 showing the frame of FIG. 1 attached to the splint.
Figure 4:
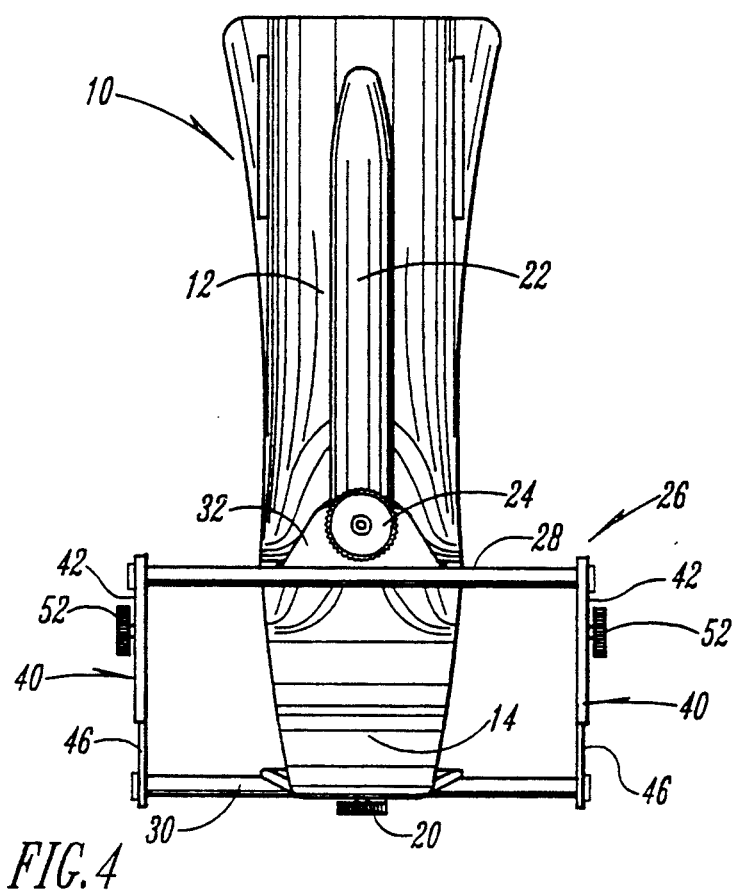
FIG. 4 is a rear elevational view of a device shown in FIG. 3.

The plastic splint 10 has all the characteristics of the plastic splint disclosed in U.S. Pat. No. 3,976,059. The splint 10 includes a back portion 12, a heel portion 14, and a foot portion 16. As described in the aforesaid patent, the heel portion 14 has a curvature greater than the normal curvature of a patient's heel to provide space between the heel of the patient and the heel portion 14. A toe bracket 18 is secured to the foot portion 16 by nut and bolt assembly 20. A stabilizer arm 22 is pivotally secured to the back portion 12 by means of nut and bolt assembly 24. The structure thus described is revealed in the above United States Patent and the structure does not of itself constitute the essence of the present invention.

The frame 26 shown in FIG. 1 constitutes the improvement of this invention over the splints of the prior art. Frame 26 includes an elongated rod or leg member 28 and a similar rod or foot member 30. Leg member 28 has a bracket 32 rigidly secured to the center portion thereof. Bracket 32 has an aperture 34 which is adapted to receive nut and bolt assembly 24 as the frame 26 is secured to the splint 10. Similarly, foot member 30 has bracket 36 rigidly secured thereto. Bracket 36 has aperture 38 which is adapted to be received by nut and bolt assembly 20 as the frame 26 is secured to the splint 10.

Frame 26 further comprises side members 40 which are comprised of upper or first arms 42 which have elongated grooves 44 milled therein. (See FIG. 1.) Lower or second arms 46 are slidably mounted within elongated grooves 44 of first arms 42. An elongated slot 48 is milled through first arms 42. Pins 50 are rigidly secured to second arms 46 and extend through slots 48 to receive lock nuts 52. The longitudinal or telescopic position of second arms 46 with respect to first arms 42 is determined by the slidable position of pins 50 in grooves 44. Lock nuts 52 serve to rigidly secure the second arms 46 to the first arms 42 in a plurality of different telescopic positions.

A plurality of apertures 54, preferably 6 in number, are drilled through first arms 42 at a position below the elongated slots 48. A semi-spherical detent element 56 is rigidly secured to the second arms 46 and are adapted to be seated in any one of the apertures 54 as best shown in FIG. 7.

Figure 5:
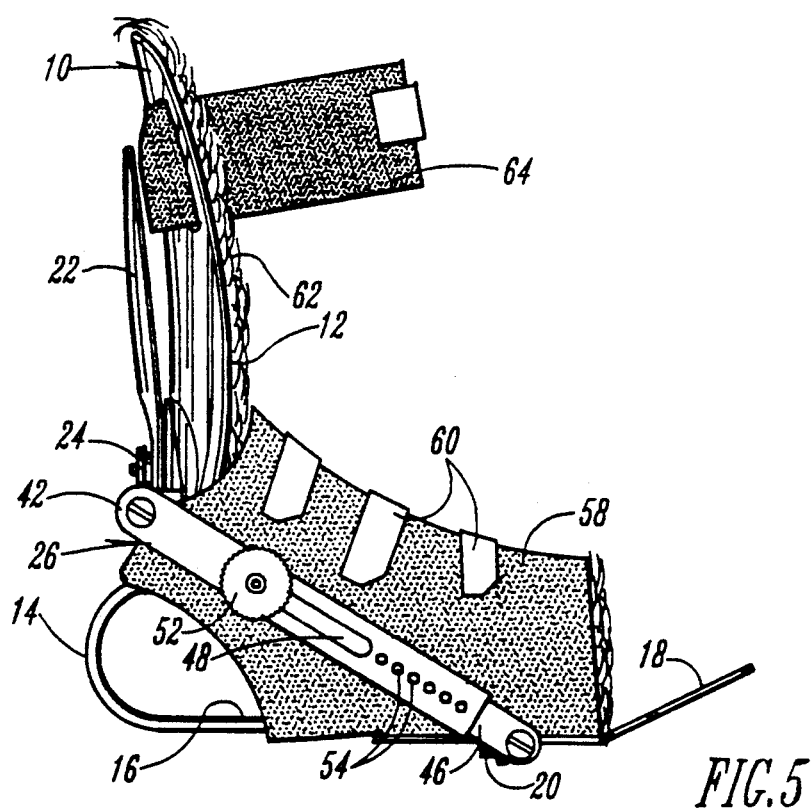
FIG. 5 is a view similar to that of FIG. 3 but shows the padding material secured to the splint of FIG. 3.

A conventional foot pad or anklet 58 is secured to splint 10 as best shown in FIG. 5. Pad 58 has a plurality of straps 60 to secure the pad to the foot of a patient wearing the splint. Leg pad 62 is positioned on one surface of back portion 12 of splint 10, and leg strap 64 serves to secure the leg of the patient to the back portion 12 of the splint 10. The pads and straps 58-64 are conventional.

When the splint 10 is applied to a patient having an extended foot drop condition, the foot portion 16 of the splint is depressed with respect to the back portion 12 as best shown in FIG. 9 to create the obtuse angular position between the foot and back portions shown by the numeral 66 in FIG. 9. This is accomplished by loosening the lock nuts 52 to permit the side members 40 to be moved to a telescopically expanded position. This permits the detent 56 on second arms 46 to move to any one of the apertures 54 which compliment the angular position of the foot of the patient being treated. The indicia means 68 adjacent the apertures 54 assist the operator in visually ascertaining the extended position of the frame 26.

The use of the detent 56 and the apertures 54 facilitates the angular extended adjustment of the frame 26. When the detent 56 slides into the appropriate aperture 54, the lock nuts 52 can be tightened to rigidly hold the frame in its predetermined position.

After the patient's foot has been held in the initial position determined by the expanded position of frame 26 for the prescribed period of time, the frame can then be moved to the next increment of angular position by loosening the nuts 52 and forcibly moving the frame to the next incremental position normally defined by moving the detent 56 to the next adjacent aperture 54.

This invention avoids any necessity of adding a plurality of plaster cast to the foot of the patient during the treatment of the drop-foot condition. It improves the process for dealing with drop-foot conditions contemplated by '059 patent by providing an adjustable frame to fix the position of deflection of the foot portion of the splint with respect to the back portion. It is therefore seen that this invention will achieve at least all of its stated objectives.

I claim:

1. A foot splint, comprising,
    a plastic splint having a back portion, a heel portion, and a foot portion,
    said foot portion being joined to said back portion by said heel portion, and normally being positioned at a substantial right angle with respect to said leg portion,
    said splint being of resilient spring-like material to permit said foot portion to be forcibly deflected at said heel portion to create an obtuse angle with respect to said leg portion,
    said back portion being adapted to engage the rearward portion of the calf of a patient's leg,
    a frame secured to said back portion above said heel portion and extending forwardly and downwardly to a point of connection with said foot portion, so as to form downwardly extending diagonal arms between said back portion and said foot portion
    expandable means on said frame to allow said frame to maintain its connection with said back and foot portions when said foot portion is moved to form an obtuse angle with respect to said leg portion,
    and lock means on said frame to rigidly hold said foot portion in an obtuse angular relationship with respect to said leg portion.

2. The foot splint of claim 1 where said frame is rectangular in shape and is comprised of parallel spaced rods connected to the back of said back portion and the bottom of said foot portion, respectively; and parallel spaced length-adjustable side members connecting said rods.

3. The foot splint of claim 1 wherein said frame is substantially rectangular in shape and has parallel spaced leg and foot members secured to said leg and foot portions, respectively, and parallel side members connecting said leg and foot members, said expandable means comprising a part of said side members.

4. The foot splint of claim 3 wherein said side members comprises first and second arm members telescopically secured together, and said lock means is operatively connected to said first and second arm members.

5. The foot splint of claim 4 wherein said second arm members have a detent element adapted for engagement with one of a plurality of detent seats on said first arm members so that engagement of said detent element with one of said detent seats will define one of a plurality of obtuse angular positions between said leg portion and said foot portion.

6. The foot splint of claim 4 wherein said each of said first arm members have an elongated slot therein, pins secured to said second arm members and extending through said elongated slots and terminating in outer ends, and lock nuts on said outer ends to lock said pins in a predetermined position with said elongated slots.

7. The foot splint of claim 3 wherein said leg and foot members are pivotally secured to said side members.

* * * * *